United States Patent
Lin et al.

(10) Patent No.: US 9,622,996 B2
(45) Date of Patent: Apr. 18, 2017

(54) USE OF ADRENERGIC BETA-E-RECEPTOR BLOCKERS IN CANCER TREATMENT

(71) Applicants: Shuguang Lin, Guangzhou (CN); Meng Zheng, Guangzhou (CN)

(72) Inventors: Shuguang Lin, Guangzhou (CN); Meng Zheng, Guangzhou (CN)

(*) Notice: Subject to any disclaimer, the term of this patent is extended or adjusted under 35 U.S.C. 154(b) by 272 days.

(21) Appl. No.: 13/754,633

(22) Filed: Jan. 30, 2013

(65) Prior Publication Data
US 2013/0197091 A1 Aug. 1, 2013

(30) Foreign Application Priority Data

Jan. 30, 2012 (CN) .......................... 2012 1 0020844

(51) Int. Cl.
*A61K 31/195* (2006.01)
*A61K 31/47* (2006.01)
*A61K 31/138* (2006.01)

(52) U.S. Cl.
CPC .......... *A61K 31/195* (2013.01); *A61K 31/138* (2013.01); *A61K 31/47* (2013.01)

(58) Field of Classification Search
CPC ..... A61K 31/195; A61K 31/138; A61K 31/47
USPC .................................................. 514/567, 657
See application file for complete search history.

(56) References Cited

PUBLICATIONS

Perrone et al, Methods in Enzymology, 2010, 484, 197-230.*
Sanchez et al, Proc. Natl. Acad. Sci, 1997, 94, 4626-4630.*
Bing et al, Intl. J. Obesity, 2010, 34, 1559-1565.*
Dou et al, Zhonghua Xueyexue Zazhi, 2004, 25(11), 675-678, SciFinder Scholar English Translation of Abstract used.*
Rickardson et al, Cancer Chemother. Pharmacol., 2006, 58, 749-758.*
Moody et al ( Handbook of Biologically Active Peptides, 2006, 473-477).*
Pasquier et al (Oncotarget, 2011, 2, 797-809).*
Rouget et al ( Biol. Reproduct.,2005, 74, 209-216).*
Ham et al (Clinical & Experimental Metastasis, 2004, 473-477).*
Brockunier et al (Bioorganic & Medicinal Chemistry Letters, 2000, 10, 2111-2114).*
Perrone (Methods in Enzymology, 2010, 484, 197-230, cited in the previous Office Action).*

* cited by examiner

*Primary Examiner* — Jason Sims
*Assistant Examiner* — Ibrahim D Bori
(74) *Attorney, Agent, or Firm* — Muncy, Geissler, Olds & Lowe, P.C.

(57) ABSTRACT

A method for treating an cancer disease is disclosed comprising administering to a subject a pharmaceutical composition comprising an adrenergic beta-3-receptor blocker.

1 Claim, 9 Drawing Sheets

5-CFDA(MRP1 substrate)

BRL

SR

USE OF ADRENERGIC BETA-E-RECEPTOR BLOCKERS IN CANCER TREATMENT

CROSS-REFERENCE TO RELATED APPLICATION

The present invention claims priority from Chinese application number 201210020844.3 filed on Jan. 30, 2012, the disclosure of which is incorporated herein by reference.

FIELD OF THE INVENTION

The present invention relates to a new usage of adrenergic beta-3-receptor (ADRB 3) blockers, and in particular to its usage in treatment of cancers or other diseases.

BACKGROUND OF THE INVENTION

Adrenergic beta-3-receptor, also known as beta-3 adrenergic receptor or beta-3 adrenoreceptor, a beta-adrenergic receptor, is located mainly in adipose tissue and is involved in the regulation of lipolysis and thermogenesis. ADRB 3 activating drugs could theoretically be used as weight-loss agents, but are limited by the side effect of tremors. Some ADRB 3 agonists have demonstrated antistress effects in animal studies, suggesting they also have a role in the CNS. Beta-3 receptors are found in gallbladder, urinary bladder, and in brown adipose tissue. Their role in gallbladder physiology is unknown, but they are thought to play a role in lipolysis and thermogenesis in brown fat. Our search did not reveal any reports about potential effect of beta-3 receptors in genesis and development of malignant tumors.

Anti-oncogene TP53 plays a key role in repair of DNA damage and in cell cycle. TP53 is a senescence-related gene, the tumor suppression effect of which closely relates to senescence. TP53 controls cell senescence through DNA damage repair, free radical generation and scavenging and other mechanisms. SIRT1 is an enzyme that deacetylates proteins, such as p53, inhibiting transcriptional activity, and thus plays a key role in p53 mediated aging and anti-tumor reactions. Mammalian target of rapamycin, also known as mTOR, plays an importance role in many aspects including cell growth, cell proliferation, cell cycle as well as tumor progression.

SUMMARY OF THE INVENTION

In the work leading to the present invention, the inventors surprisingly found that the adrenergic beta-3-receptor (hereinafter sometimes referred to as the β3 receptor) is a key receptor involved in regulation of signaling pathways of SIRT1, p53, mTOR and microRNA-16. Based on this finding, the present invention provides a new usage of adrenergic β3 receptor blockers in treating mTOR/SIRT1/p53 signaling pathways related diseases, including malignant tumors, pulmonary hypertension, atherosclerosis, hypertrophic cardiomyopathy and etc. The present invention further provides a new usage of adrenergic β3 receptor blockers in treatment of tumors by serving as a dual inhibitor of microtubules and mTOR. It is also found that adrenergic β3 receptor blockers and siRNA thereof are able to reduce SIRT1 expression in tumors and their peripheral adipose tissues, resulting in acetylation of p53 and in turn enhancement of transcriptional activity thereof. The expression of p53 in tumors is thus increased, promoting tumor cell senescence, apoptosis and preventing tumor metastasis. Adrenergic β3 receptor blockers are also found to inhibit production of ATP while increasing reactive oxygen species (ROS) by promoting mitophagy to reduce number of mitochondrion in tumor cells. Experiments also demonstrate that adrenergic β3 receptor blockers promote cell apoptosis and autophagic cell death by upregulation of miR-16-1 and miR-15a in HL-60 leukaemia cell lines.

The anti-tumor effect of β3 receptor blockers is achieved by at least one of the following mechanisms, (a) increase in mitophagy, reduction in mitochondrial membrane potential, suppression of voltage-dependent anion channel (VDAC), and increase in reactive oxygen species; (b) suppression of Rheb/SIRT1/FOXO4 pathway, enhancing acetylation of p53; (c) inhibition of p62/mTORC2/4EBP1 pathway, reduction in binding of mTORC2 to α-Tubulin, and prevention of binding of phosphorylated mTOR (Ser2448) to centrosomes at both poles of spindle apparatus; (d) damage to spindle apparatus to suppress mitosis; (e) inhibition of hypoxia inducible factor-1α(HIF1α)/hexokinase II pathway to reduce glycolysis; (f) inhibition of multidrug resistance-associated protein 1 (MRP1); and (g) upregulation of expression of miR-16-1 and miR-15a.

The β3 receptor blockers used in the present invention include any compound that is able to inhibit or block the β3 receptor. Representative agonists suitable for use in the present invention include but not limited to SR59230A having a formula shown in FIG. 18. It is expected that compounds that have SR59230A as nucleus are suitable for use with the present invention.

The β3 receptor blockers used in the present invention can be prepared by conventional methods and provided in suitable form, including tablets, capsules, granules, controlled release formulations, injectable formulations and others.

The present invention propose to use β3 receptor antagonists as drugs or a part of drugs for treating malignant tumors, pulmonary hypertension, atherosclerosis, hypertrophic cardiomyopathy and etc.

The present invention revealed signaling pathway of adrenergic β3 receptor in regulation of expression and activity of mTOR, SIRT1 and p53 proteins, which is very meaningful to research of genesis and development of tumors, metabolic diseases, immune system diseases and aging-related disease. The beta-3 adrenergic receptor can be served as a target to treat those diseases by regulation of the receptor.

DETAILED DESCRIPTION OF THE INVENTION

Definitions

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" include any and all combinations of one or more of the associated listed items. It will be further understood that the terms "comprises" "comprising" "includes" and/or "including" when used herein, specify the presence of stated features, integers, steps, operations, elements, and/or components, but do not preclude the presence or addition of one or more other features, integers, steps, operations, elements, components, and/or groups thereof.

An "beta-3 adrenergic receptor blocker", also known as beta-3 adrenergic receptor blocking agent or antagonist, is a compound that capable of interfering with the binding to the β3 receptor. It is contemplated that compounds meet the definition are usable with the present invention, preferably selective antagonist of the beta-3 receptor, such as SR 59230A.

EXAMPLES

Example 1

Figure 1:
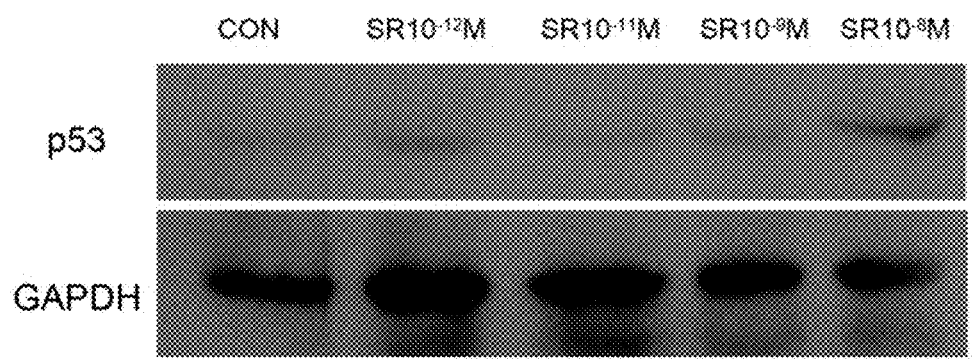
FIG. 1. SR59230A increased expression level of p53 in MCF-7 cells.
Figure 2:
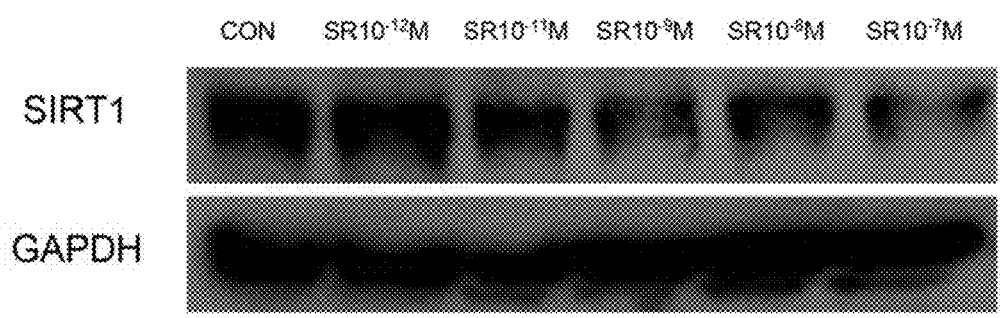
FIG. 2. SR59230A decreased expression level of SIRT1 in MCF-7 cells.

MCF-7 cells were treated with SR59230A at different concentrations. After 24 h, the cells were lysed to extract total protein. The protein concentration was determined by BCA method. 10 μg of the protein was used to perform 10% SDS PAGE, and then transferred to a PVDF membrane. The membrane was blocked for 1 h with TBST (10 mmol/L Tris HCl, pH 7.5, 150 mmol/L NaCl, 0.1% Tween 20) containing 4% fat-free milk, and incubated overnight with p53 antibody (1:1000) and SIRT1 antibody (1:1000) at 4° C. The membrane was further incubated with secondary antibodies for 1 h after washing, followed by ECL color development. The same procedure was repeated 3 times. The gray values of protein bands were obtained through Fluorchem 8900 software and the ratio of target band to reference band (GAPDH) was calculated. Results are shown in FIGS. 1 and 2, wherein the expression level of p53 was increased as the increase of SR59230A concentration, while SIRT1 was decreased.

Example 2

Figure 3:
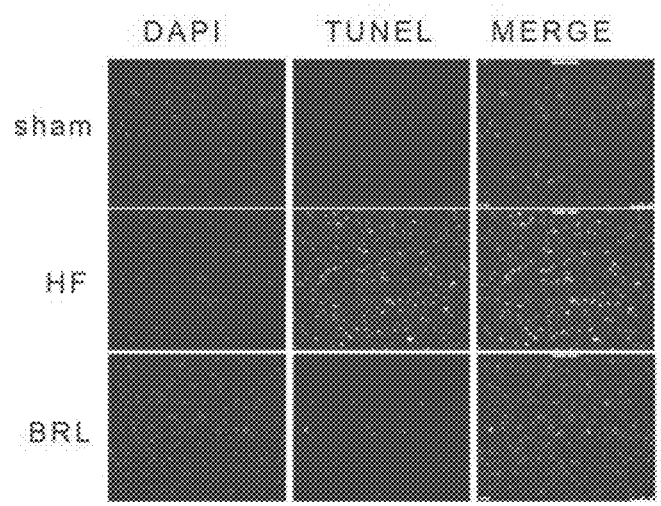
FIG. 3. BRL37344 decreased cardiomyocytes apoptosis of heart failure rats.
Figure 4:
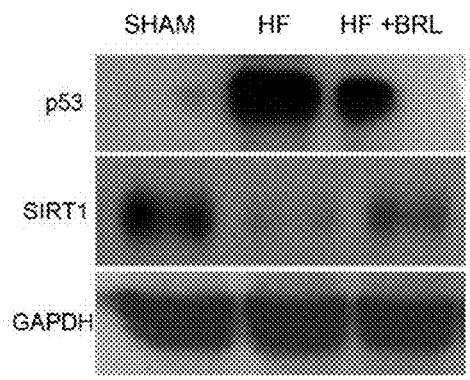
FIG. 4. BRL37344 decreased p53 level in cardiac muscle and increased SIRT1.
Figure 5:
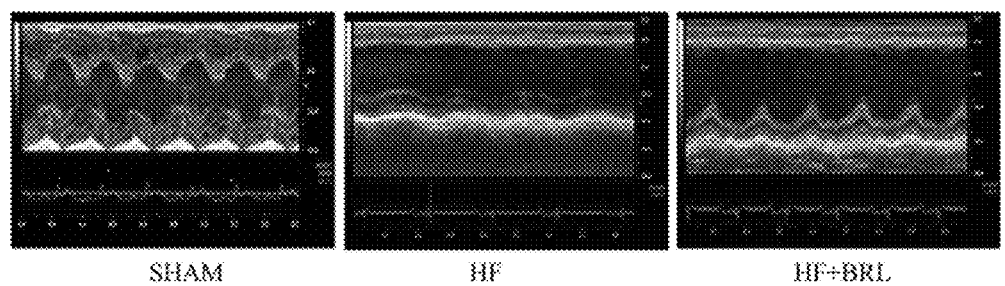
FIG. 5. BRL37344 improved cardiac function of heart failure rats.

In rat myocardial infarction models, activation of the β-3 receptor could increase level of SIRT1 in cardiomyocyte, inhibit expression of p53, improve the cardiac function and achieve anti-apoptosis effect. The myocardial infarction model was created by ligation of anterior descending branch of rat left coronary artery. BRL37344 was intraperitoneally injected at 1 mg/kg/day, and heart B-ultrasonography was performed after 4 weeks. Heart tissue was determined for apoptosis (tunel method) and expression levels of SIRT1 and p53 (western blot). The ratio of left ventricular weight to body weight (LVW/BW) is determined. It can be seen from the results shown in FIGS. 3 to 5, that BRL37344 decreases p53 expression, cardiac cell apoptosis, and value of LVW/BW of heart failure rat, increases SIRT1 expression, alleviate cardiac hypertrophy and improve cardiac function.

Example 3

Figure 6:
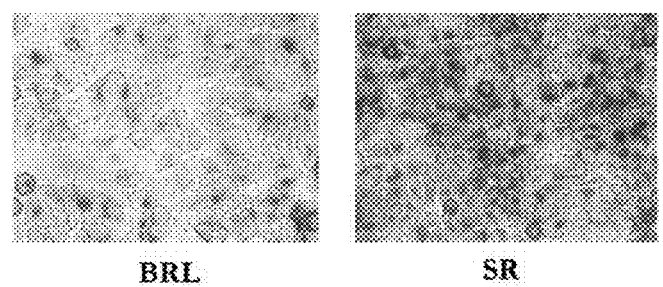
FIG. 6. Staining of β-galactosidase in adipose-derived stem cells.

Blockage of the β-3 receptor could increase level of β-galactosidase in adipose-derived stem cells and promote stem cell aging. BRL37344 and SR59230A were used to treat adipose-derived stem cells of rats each at $10^{-7}$M. After 24 h, cells were fixed using paraformaldehyde, and stained and photographed according to the specification of β-Galactosidase Staining Kit. Results were shown in FIG. 6. BRL37344 decreased the level of β-galactosidase in adipose-derived stem cells when compared with SR59230A, indicating agonisting of adrenergic β3 receptors of adipose-derived stem cells achieves anti-aging effect.

Example 4

Figure 7:
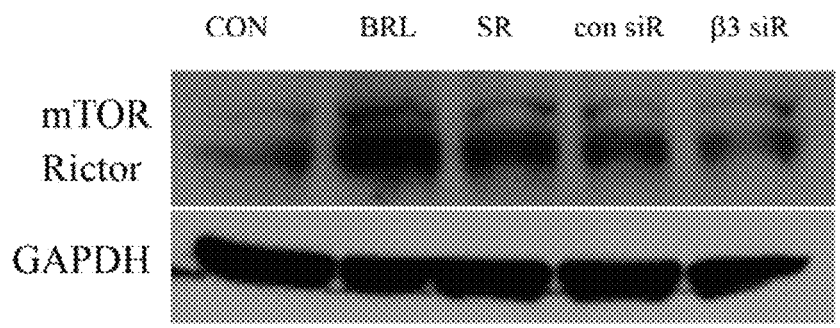
FIG. 7. BRL37344 increased level of mTOR/Rictor complex.

Activation of the β3 receptor could increase mTOR/Rictor complex in MCF-7 cells. shRNA of β3 adrenergic receptor, control shRNA, BRL37344 and SR59230A were used to treat rat cardiomyocyte each at $10^{-7}$M. After 24 h, total protein was extracted and subjected to western blot to determine the expression amount of mTOR and Rictor proteins. The results were shown in FIG. 7. BRL37344 increased Mtor/Rictor complex while β3 adrenergic receptor shRNA significantly decreased mTOR/Rictor complex, when compared to the control shRNA.

Example 5

Figure 8:
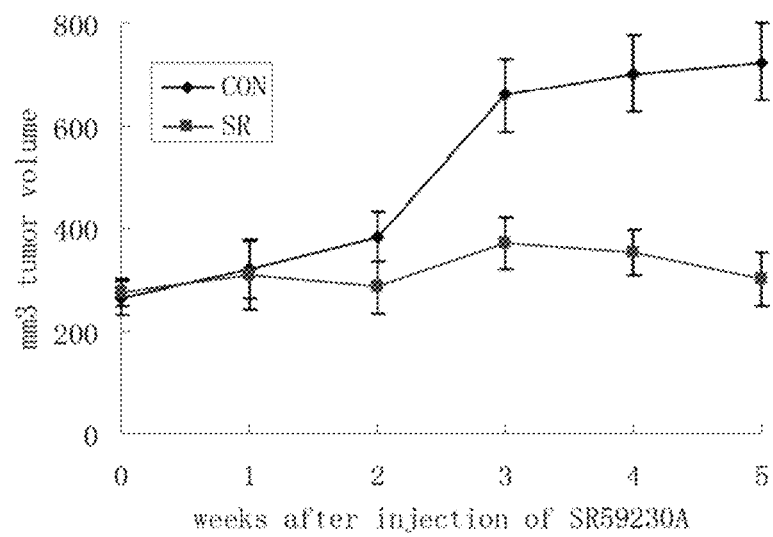
FIG. 8. Tumor growth curve of naked rats.
Figure 9:
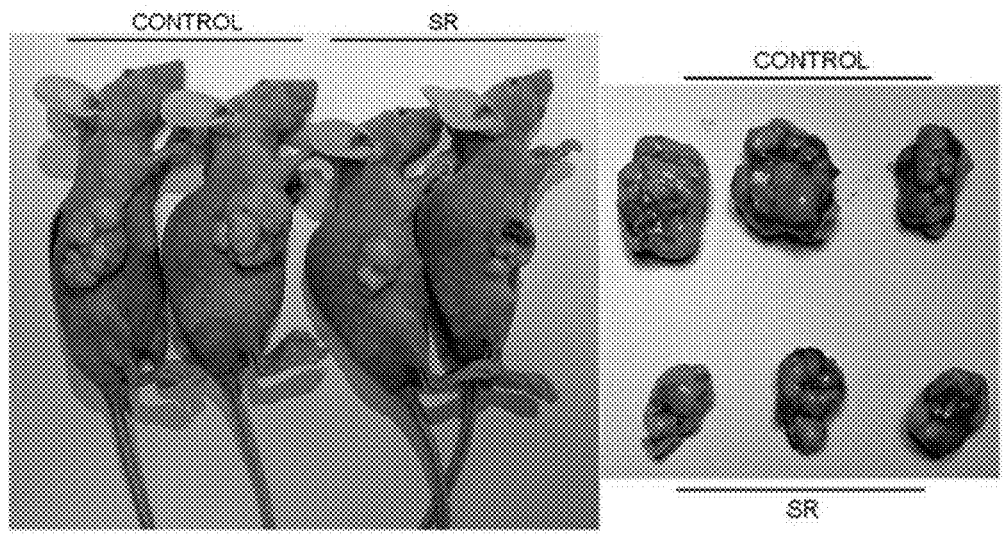
FIG. 9. SR59230A suppressed tumor growth in nude mice.

SR59230A reduced implant tumor volume in MCF-7 nude mice. $10^7$ of MCF-7 cells were subcutaneously injected into 5-week old female nude mice to establish implant tumor model. 10 days followed the injection, tumor volume increased to about 250 mm$^3$. The mice were randomly divided into two groups with each group having 8 mice. The treatment group was peritoneally injected with SR56230A at 100 nmol for each mouse. The injection was carried every two days and lasted for 5 weeks. The control group is administrated with solvents with same volume. The length, width and height of tumors were determined using a vernier caliper prior to each administration, so as to calculate tumor volume. The tumor growth curve was shown in FIG. 8, in which SR59230A treated mice had slower implant tumor growth rat when compared to control group (FIG. 9).

Figure 10:
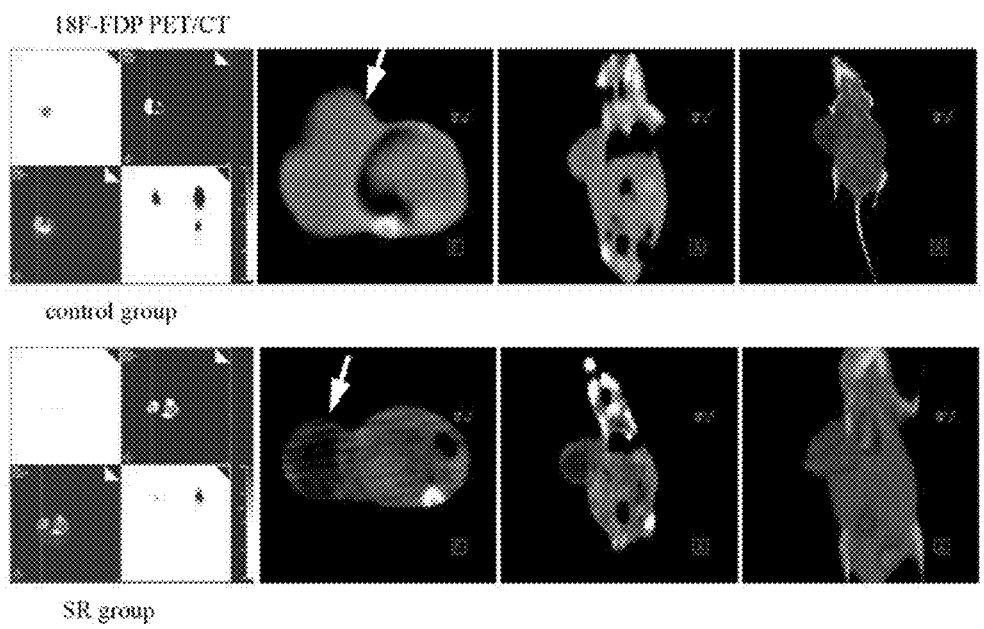
FIG. 10. SR59230A suppressed glycolysis in tumors of nude mice.
Figure 11:
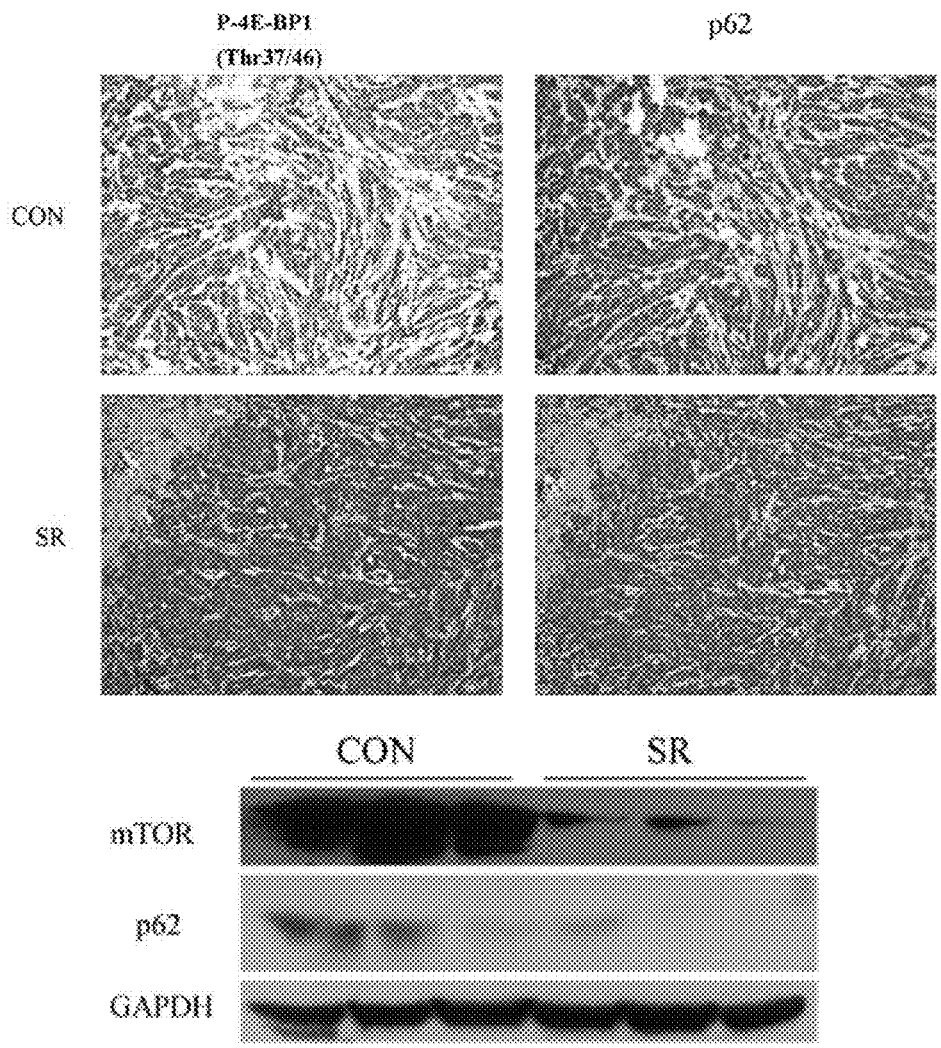
FIG. 11. SR59230A suppressed mTOR activity in tumors of nude mice.
Figure 12:
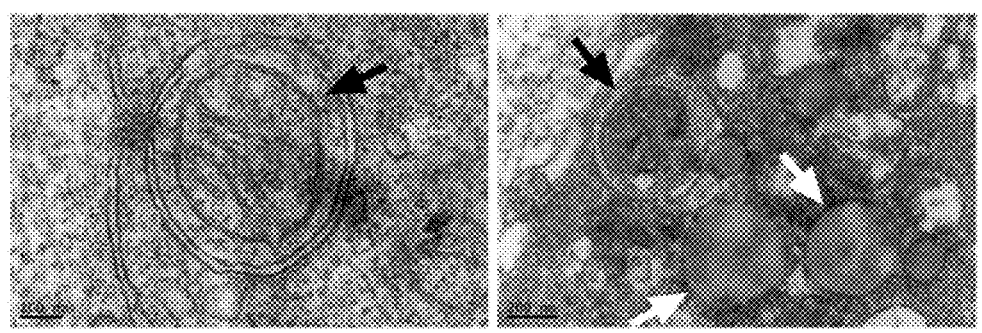
FIG. 12. SR59230A increased mitophagy in tumors of nude mice.

SR59230A treated group has a tumor volume of 42.03% based on the control group, a tumor inhibition rate of 57.97%, and a relative tumor growth rate T/C (%) of 39.80%. 18F-FDP PET/CT detection showed SR59230A inhibited glycolysis (FIG. 10). In order to determine expression levels of phospho-4E-BP1(Thr37/46) and p62, the tumor tissue was obtained for paraffin embedding and section and then immunohistochemistry, and proteins were extracted from the tumor tissue for Western blot. The results showed SR59230A inhibited mTOR activity and reduced expression of phospho-4E-BP1 and p62 (FIG. 11). Tumor tissue, when observed under transmission electron microscope, showed SR59230A enhanced mitophagy in tumor cells (FIG. 12).

Example 6

Figure 13:
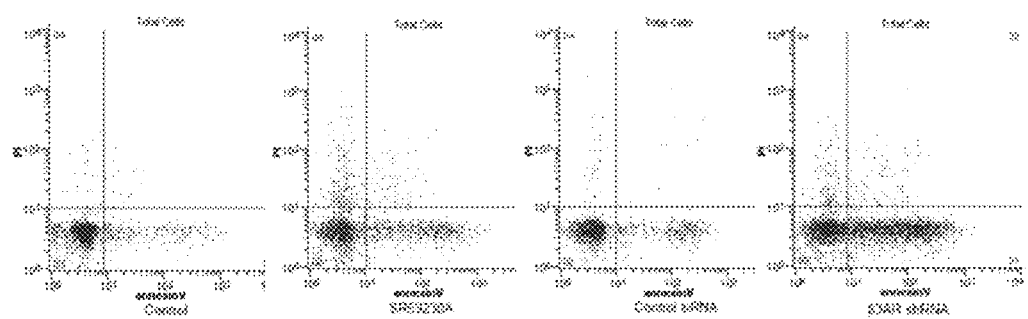
FIG. 13. Annexin V/PI flow cytometry.

SR59230A and β3 receptor-targeted siRNA promoted apoptosis of MCF-7 breast carcinoma cells, H1975 and H1299 lung cancer cells. A target sequence was selected from the DNA sequence of β3AR gene using computer program. The DNA fragment of the target sequence was synthesized and cloned on a vector. Human U6 promoter was cloned to pcDNA3/neo vector to clone DNA fragment of shRNA. The plasmid vector was tranfected into cells using lipofection2000. 48 h following the tranfection, siRNA was expressed in the cells. The cells were subjected to Annexin V/PI double staining. Apoptosis rate was determined by flow cytometry. As shown in FIG. 13, silencing of β3AR gene increased apoptosis rate of MCF-7 cells (51.1±9.3% vs 19.5±4.4%, P<0.01) and increase G1-phase cells (72.6±4.2% vs 38.5±3.5%, P<0.01). SR59230A group had a significant increase in apoptosis rate than control group (P<0.01). Similar results were obtained on H1975 and H1299 lung cancer cells, i.e., SR59230A and β3 receptor-targeted siRNA promoted apoptosis of H1975 and H1299 cells. The forward sequences of β3 receptor-targeted siRNAs were shown in Table 1

TABLE 1

Forward sequences of β3 receptor-targeted siRNAs

| No. | Nucleotide Sequences |
| --- | --- |
| 1 | 5'-ctggctaggttatgccaat-3' |
| 2 | 5'-cagctctcttgccccatgg-3' |
| 3 | 5'-cagctctcttgccccatgg-3' |
| 4 | 5'-taccg ccaacaccagtggg-3' |
| 5 | 5'-cgtgttcgtgacttcgctg-3' |
| 6 | 5'-ccgcgctgctgtgccttc-3' |
| 7 | 5'-ggggtgcccgcctgcggcc-3' |
| 8 | 5'-caccgggccctgtgcacct-3' |

Example 7

Figure 14:
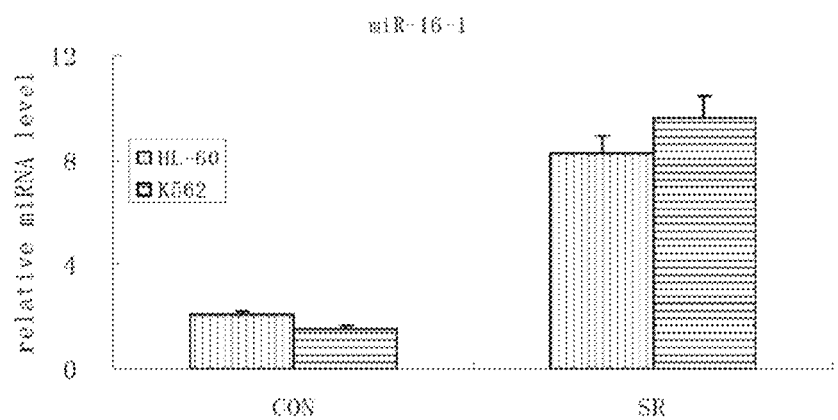
FIG. 14. SR59230A increased miR-16-1 in HL-60 and K562 leukaemia cell lines.
Figure 15:
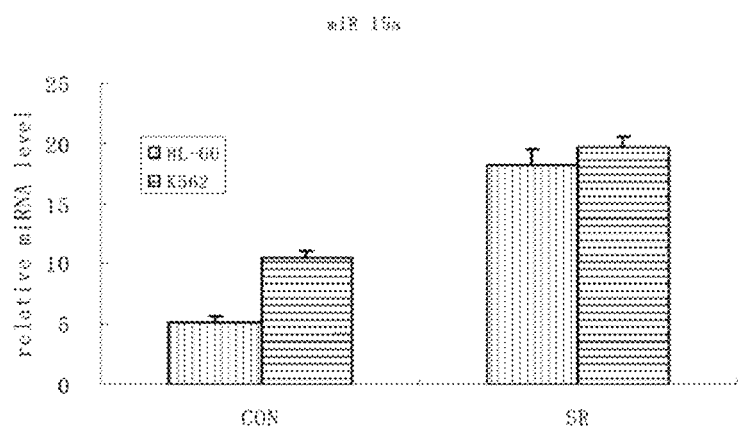
FIG. 15. SR59230A increased miR-15a in HL-60 and K562 leukaemia cell lines.
Figure 16:
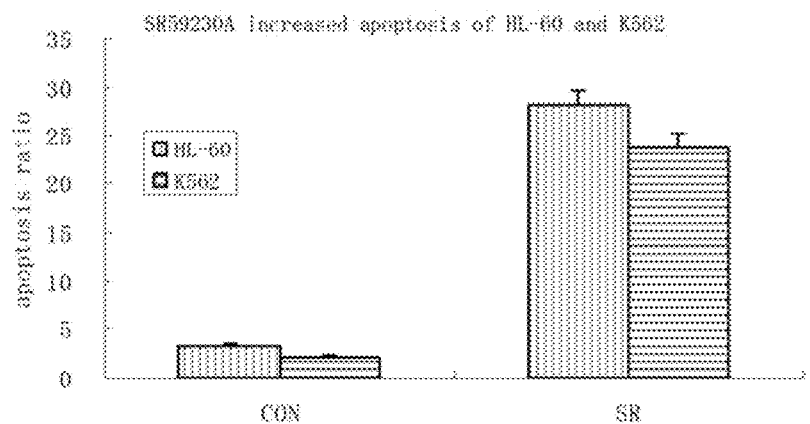
FIG. 16. SR59230A increased apoptosis of HL-60 and K562 leukaemia cells.
Figure 17:
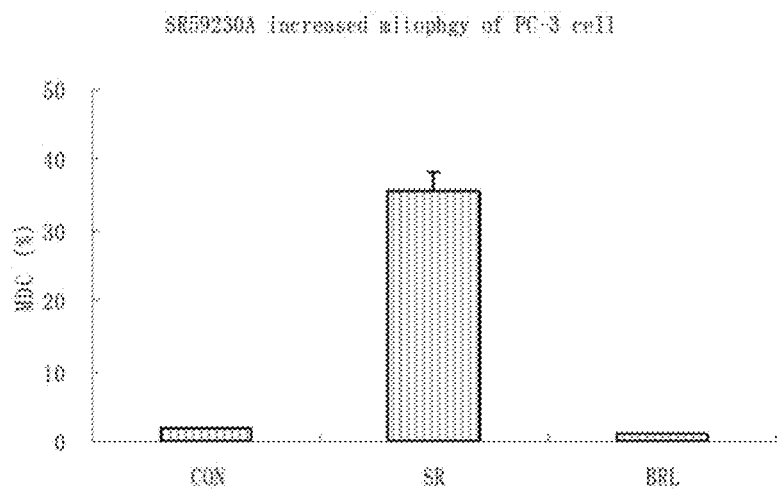
FIG. 17. SR59230A increased autophagy of prostatic cancer cells PC-3.
Figure 18:
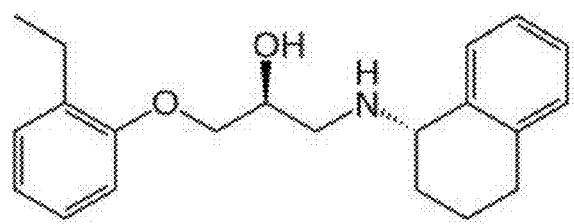
FIG. 18. Formula structure of SR59230A.

SR59230A promoted cell apoptosis by increase expression of miR-16-1 and miR-15a in HL-60 and K562 leukaemia cells. SR59230A at $10^{-7}$M was used to treat HL-60 and K562 leukaemia cells. 8 h following the treatment, total microRNA was extract and then reversely transcribed for quantitative PCR to determine the expression of miR-16-1 and miR-15a. Flow cytometry was used to detect earlier cell apoptosis label Annexin V/PI and apoptosis rate. MitoTracker Red CMXRos was used to detect number of mitochondrion. JC1 was used to determine mitochondrial membrane potential. Autophagosome was determined by monodansylcadaverine (MDC) staining, and observed and countered under transmission electron microscope. Intracellular ATP level was determined by ATP Kit. The results were shown in FIGS. 14 to 16, in which SR59230A significantly increased expression of miR-16-1 and miR-15a in HL-60 and K562 leukaemia cells and increased apoptosis rate (*P<0.01), compared to the control group. SR59230A could decrease mitochondrial membrane potential of HL-60 and K562 cells, induce mitophagy, decrease mitochondrial content and reduce intracellular ATP level.

Figure 19:
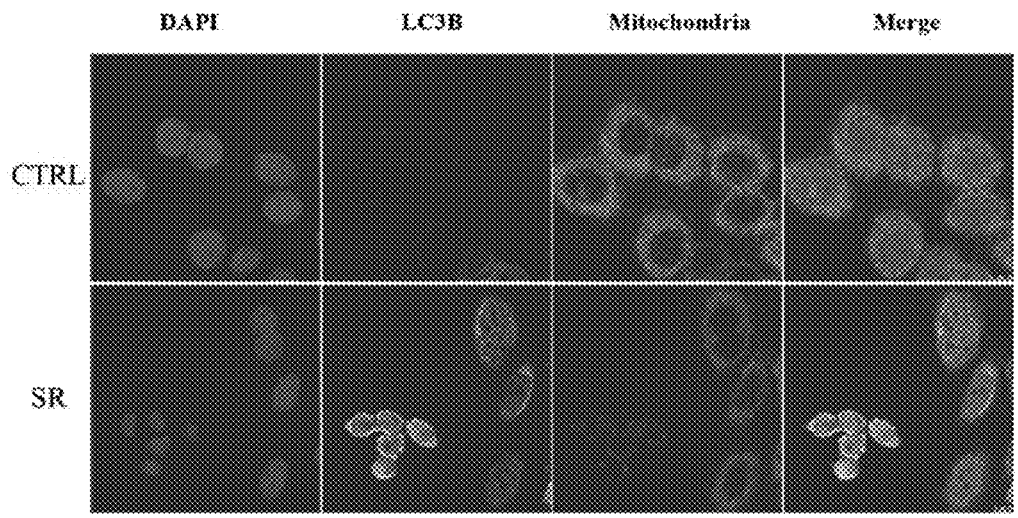
FIG. 19. Results of immunofluorescence double staining of MitoTracker/LC3B.

Example 8

β3 receptor regulated mitochondrial autophagy. MCF7 cells were treated by SR59230A ($10^{-7}$M) for 18 h. MitoTracker was used to label mitochondrion at 37° C. for 20 min. The cells were washed with PBS for 3 times and fluorescent detection was then carried out by fluorescent confocal microscopy and flow cytometry. The autophagy labeling protein LC3II was measured by Western blot. The results showed SR59230A significantly decreased mitochondrion amount, increased autophagosome, and increased LC3II expression (FIG. 19).

Example 9

Figure 20:
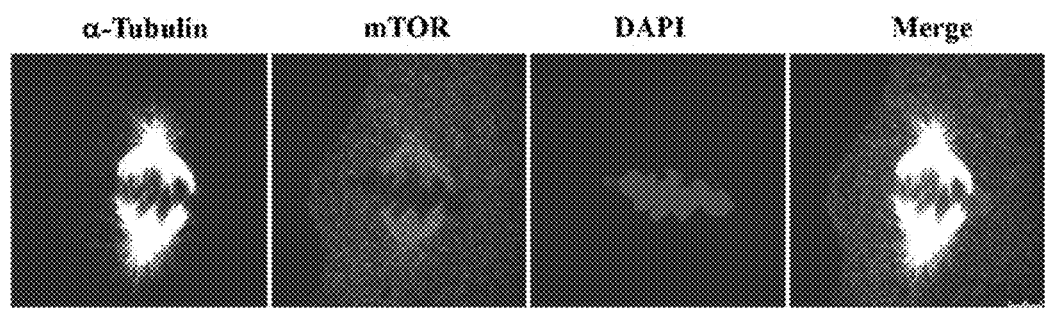
FIG. 20. Results of immunofluorescence double staining of mTOR/α-Tubulin.
Figure 21:
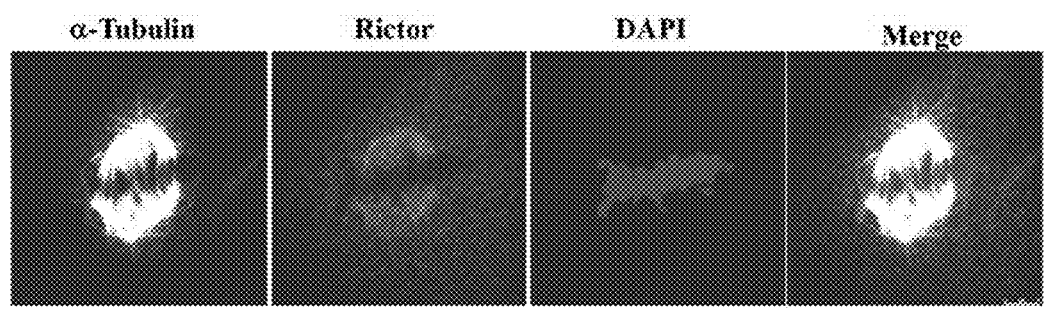
FIG. 21. Results of immunofluorescence double staining of Rictor/α-Tubulin.

Beta-3 receptor promoted binding of mTORC2 to α-Tubulin in spindle apparatus. BRL37344 was used to treat cardiac fibroblast of rats at $10^{-7}$M. The cells were undergone mTOR/α-Tubulin immunohistochemical double staining and Rictor/α-Tubulin immunohistochemical double staining, and observed under confocal microscope. The results showed BRL37344 promoted binding of mTOR to α-Tubulin in spindle apparatus (FIG. 20) and Rictor to α-Tubulin (FIG. 21).

Example 10

Figure 22:
FIG. 22. Results of 5-CFDA staining.
Figure 22:
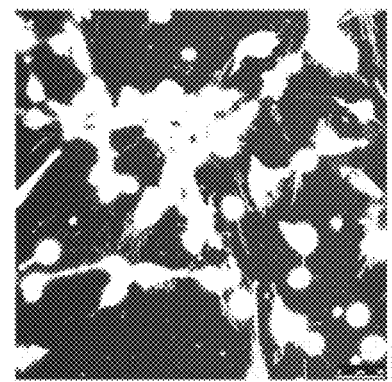

Beta-3 receptor activated multidrug resistance-associated protein 1 (MRP1). Human prostatic cancer cells PC-3 was used to be treated with SR59230A and BRL37344, each at $10^{-7}$M, for 18 h and then stained with substrate of MRP1, 5-CFDA and observed under confocal microscopy. The results showed SR59230A inhibited 5-CFDA efflux (FIG. 22), indicating SR59230A inhibited MRP1 and was able to improve efficiency of anti-cancer drugs.

It should be understood that various example embodiments have been described with reference to the accompanying drawings in which only some example embodiments are shown. The present invention, however, may be embodied in many alternate forms and should not be construed as limited to only the example embodiments set forth herein.

What is claimed is:
1. A method for treating breast cancer comprising administering to a subject in need of the treatment, a pharmaceutical composition comprising a selective adrenergic beta-3-receptor blocker; wherein said selective adrenergic beta-3-receptor blocker is SR59230A.

* * * * *